(12) United States Patent
Ahn et al.

(10) Patent No.: US 10,092,679 B2
(45) Date of Patent: Oct. 9, 2018

(54) LAMINOUS VASCULAR CONSTRUCTS COMBINING CELL SHEET ENGINEERING AND ELECTROSPINNING TECHNOLOGIES

(71) Applicant: Wake Forest University Health Sciences, Winston-Salem, NC (US)

(72) Inventors: Hyunhee Ahn, Winston-Salem, NC (US); Young Min Ju, Winston-Salem, NC (US); Anthony Atala, Winston-Salem, NC (US); Sang Jin Lee, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 425 days.

(21) Appl. No.: 14/518,352

(22) Filed: Oct. 20, 2014

(65) Prior Publication Data
US 2015/0112419 A1   Apr. 23, 2015

Related U.S. Application Data

(60) Provisional application No. 61/892,866, filed on Oct. 18, 2013.

(51) Int. Cl.
| A61L 27/50 | (2006.01) |
| --- | --- |
| A61L 27/26 | (2006.01) |
| A61F 2/07 | (2013.01) |
| A61L 27/38 | (2006.01) |
| A61F 2/06 | (2013.01) |
| C12N 5/071 | (2010.01) |
| D01D 5/00 | (2006.01) |

(52) U.S. Cl.
CPC .............. *A61L 27/507* (2013.01); *A61F 2/06* (2013.01); *A61F 2/062* (2013.01); *A61F 2/07* (2013.01); *A61L 27/26* (2013.01); *A61L 27/3808* (2013.01); *A61L 27/3826* (2013.01); *C12N 5/0691* (2013.01); *A61F 2210/0076* (2013.01); *A61F 2240/001* (2013.01); *C12N 2533/40* (2013.01); *C12N 2533/54* (2013.01); *D01D 5/0007* (2013.01)

(58) Field of Classification Search
None
See application file for complete search history.

(56) References Cited

U.S. PATENT DOCUMENTS

| 5,281,422 A | 1/1994 | Badylak et al. |
| --- | --- | --- |
| 5,645,532 A | 7/1997 | Horgan |
| 5,656,478 A * | 8/1997 | Tanagho ............... C12N 5/0661 424/93.7 |
| 5,698,271 A | 12/1997 | Liberti et al. |
| 5,855,610 A | 1/1999 | Vacanti et al. |
| 5,922,028 A | 7/1999 | Plouhar et al. |
| 6,009,832 A | 1/2000 | Innings et al. |
| 6,099,832 A | 8/2000 | Mickle et al. |
| 6,143,293 A | 11/2000 | Weiss et al. |
| 6,171,344 B1 | 1/2001 | Atala |
| 6,428,802 B1 | 8/2002 | Atala |
| 6,471,993 B1 | 10/2002 | Shastri et al. |
| 6,530,956 B1 | 3/2003 | Mansmann |
| 6,537,567 B1 | 3/2003 | Niklason et al. |
| 6,592,623 B1 | 7/2003 | Bowlin et al. |
| 6,596,296 B1 | 7/2003 | Nelson et al. |
| 6,649,159 B2 | 11/2003 | Yang et al. |
| 7,179,287 B2 | 2/2007 | Wolfinbarger, Jr. |
| 7,531,503 B2 | 5/2009 | Atala et al. |
| 7,622,299 B2 | 11/2009 | Sanders et al. |
| 2002/0028243 A1 | 3/2002 | Masters |
| 2002/0034476 A1 | 3/2002 | Lauffer et al. |
| 2002/0081732 A1 | 6/2002 | Bowlin et al. |
| 2002/0087174 A1 | 7/2002 | Capello |
| 2002/0090725 A1 * | 7/2002 | Simpson ................ A61L 15/32 435/402 |
| 2003/0021821 A1 | 1/2003 | Fertala et al. |
| 2003/0097180 A1 | 5/2003 | Tormala et al. |
| 2003/0100830 A1 | 5/2003 | Zhong et al. |
| 2003/0219417 A1 | 11/2003 | Wolfinbarger |
| 2004/0005297 A1 | 1/2004 | Connelly et al. |
| 2004/0009600 A1 * | 1/2004 | Bowlin ..................... A61F 2/08 435/395 |

(Continued)

FOREIGN PATENT DOCUMENTS

| DE | 2917037 B1 | 4/1980 |
| --- | --- | --- |
| DE | 19919625 A1 | 11/2000 |

(Continued)

OTHER PUBLICATIONS

Ju et al (Biomaterial May 2010; 31(15)4313-21).*
Australian Search Report received in Application No. 2006223063, dated Oct. 19, 2010; 3 pages.
Australian Office Action received in Application No. 2006223112, dated Sep. 30, 2010; 5 pages.
Ballou et al., "Noninvasive Imaging of Quantum Dots in Mice", Bioconjugate Chem., 2004 vol. 15, pp. 79-86.
Bull et al., Nano Lett., 2005, vol. 5 (1), pp. 1-4.

(Continued)

*Primary Examiner* — Leon B Lankford, Jr.
(74) *Attorney, Agent, or Firm* — Thomas J. Engellenner; Reza Mollaaghababa; Pepper Hamilton LLC

(57) ABSTRACT

Vascular scaffolds and methods of fabricating the same are disclosed for tissue engineering of vascular constructs. By combining electrospun matrices with cell sheet technologies, vascular constructs with more mature cell layers can be obtained for reconstruction of blood vessels, heart valves and the like. A engineered smooth muscle cell sheet, wrapped around an electrospun vascular scaffold, is able to provide a mature SMC layer that expresses strong cell-to-cell junction markers and contractile proteins. In addition, preconditioning of the cell sheet covered vascular scaffold maintained cell viability and infiltration into the scaffold.

27 Claims, 8 Drawing Sheets

(56) References Cited

U.S. PATENT DOCUMENTS

| | | | |
|---|---|---|---|
| 2004/0024946 A1 | 2/2004 | Naumann et al. | |
| 2004/0037813 A1 | 2/2004 | Simpson et al. | |
| 2004/0044403 A1 | 3/2004 | Bischoff et al. | |
| 2004/0093081 A1 | 5/2004 | Nilsson et al. | |
| 2004/0110439 A1 | 6/2004 | Chaikof et al. | |
| 2004/0117033 A1 | 6/2004 | Frondoza et al. | |
| 2004/0146546 A1 | 7/2004 | Gravett et al. | |
| 2004/0249464 A1 | 12/2004 | Bindseil et al. | |
| 2005/0095695 A1 | 5/2005 | Shindler et al. | |
| 2005/0142161 A1 | 6/2005 | Freeman et al. | |
| 2005/0266067 A1 | 12/2005 | Sengupta et al. | |
| 2006/0154063 A1 | 7/2006 | Fujihara et al. | |
| 2006/0204441 A1 | 9/2006 | Atala et al. | |
| 2006/0204445 A1 | 9/2006 | Atala et al. | |
| 2006/0204539 A1 | 9/2006 | Atala et al. | |
| 2006/0240061 A1 | 10/2006 | Atala et al. | |
| 2006/0246584 A1 | 11/2006 | Covelli | |
| 2006/0253192 A1 | 11/2006 | Atala et al. | |
| 2006/0257377 A1 | 11/2006 | Atala et al. | |
| 2007/0213801 A1 | 9/2007 | Kutryk et al. | |
| 2008/0003184 A1 | 1/2008 | Uvdal et al. | |
| 2008/0025956 A1 | 1/2008 | Yoder et al. | |
| 2010/0129450 A1 | 5/2010 | Atala et al. | |
| 2010/0190254 A1* | 7/2010 | Chian | A61L 27/3847 435/396 |
| 2014/0112973 A1* | 4/2014 | Steinberg | A61L 27/34 424/445 |
| 2014/0309726 A1* | 10/2014 | Wang | A61L 27/56 623/1.46 |

FOREIGN PATENT DOCUMENTS

| | | |
|---|---|---|
| DE | 20019928 U1 | 2/2001 |
| EP | 1405649 A1 | 4/2004 |
| EP | 1604697 A1 | 12/2005 |
| JP | 2004162244 A | 6/2004 |
| WO | 9911191 A1 | 3/1999 |
| WO | 199948541 A1 | 9/1999 |
| WO | 2001027365 A1 | 4/2001 |
| WO | 2001037884 A2 | 5/2001 |
| WO | 2001080921 A2 | 11/2001 |
| WO | 2002000149 A1 | 1/2002 |
| WO | 2002030482 A1 | 4/2002 |
| WO | 2003007790 A2 | 1/2003 |
| WO | 2004000915 A2 | 12/2003 |
| WO | 2004014304 A2 | 2/2004 |
| WO | 2004044281 A2 | 5/2004 |
| WO | 2004045425 A1 | 6/2004 |
| WO | 2004098420 A2 | 11/2004 |
| WO | 2005020849 A2 | 3/2005 |

OTHER PUBLICATIONS

Chen et al., "The Use of a PLGA Fiber/Collagen Composite Web as a Scaffold for Engineering of Articular Cartilage Tissue with Ajustable Thickness", J. Biomed Mater Res A, Dec. 15, 2003;67(4): 1170-1180.
European Office Action received in Application No. 06738128.5 dated May 6, 2008; 4 pages.
European Office Action received in Application No. 06738070.9 dated Sep. 4, 2008; 8 pages.
European Office Action received in Application No. 06738128.5 dated Oct. 15, 2010; 7 pages.
Gnasso et al., Association between wall shear stress and flow-mediated vasodilation in healthy men. Atherosclerosis, 2001, 156, pp. 171-176.
Hafemann et al.,"Use of a collagen/elastin-membrane for the tissue engineering of dermis." Burns. Aug. 1999;25(5):373-84.
Hirsch et al., "Nanoshell—Mediated Near-Infrared Thermal Therapy of Tumors Under Magnetic Resonance Guidance", PNAS, vol. 100, pp. 13549-13554, 2003.
Huang et al., "Engineered Collagen-Peo Nanofibers and Fabrics", Journal of Biomaterials Science, 2001 vol. 12, pp. 379-993.
International Search Report and Written Opinion received in PCT/US2006/009034 dated Jan. 24, 2007; 12 pages.
International Search Report and Written Opinion received in PCT/US2006/008964, dated Feb. 5, 2007; 10 pages.
International Search Report and Written Opinion received in PCT/US2006/008962 dated Feb. 20, 2007; 22 pages.
Japanese Office Action received in Application No. JP2008501058 dated Feb. 14, 2012; 8 pages.
Japanese Office Action received in Application No. JP2008501039 dated Apr. 5, 2011; 5 pages.
Klebe., "Cytoscribing: A Method for Micropositioning Cells and the Construction of Two-and Three-Dimensional Synthetic Tissues," Experimental Cell Research 179 (1988), pp. 362-373.
Liao et al., "Hierarchically Biomimetic Bone Scaffold Materials: Nano-HA/Collagen/PLA Composite", J.Biomed Mater Res B Appl Biomater May 15, 2004; 69(2): 158-165.
Magarey et al., The Blood Pressure of Sheep:, Australian Journal of Experimental Biology, Medical Science,1957, vol. 35, pp. 347-352.
Ott et al., "Sheer stress-conditioned, Endothelial Cell-Seeded Vascular Grafts: Improved Cell Adherence in Response to in Vitro Shear Stress," Surgery, Mar. 1995, pp. 334-339.
Office Action received in U.S. Appl. No. 11/083,853 dated Jul. 10, 2008; 10 pages.
Office Action received in U.S. Appl. No. 12/621,052 dated Jun. 5, 2013; 8 pages.
Office Action received in U.S. Appl. No. 12/621,052 dated Nov. 26, 2013;10 pages.
Office Action received in U.S. Appl. No. 11/372,743 dated Sep. 13, 2010; 27 pages.
Office Action received in U.S. Appl. No. 11/372,743 dated Dec. 1, 2009; 20 pages.
Office Action received in U.S. Appl. No. 11/083,602 dated Mar. 24, 2016; 12 pages.
Office Action received in U.S. Appl. No. 11/373,066 dated May 20, 2009; 11 pages.
Office Action received in U.S. Appl. No. 11/373,066 dated Mar. 27, 2014; 26 pages.
Office Action received in U.S. Appl. No. 11/083,602 dated Jan. 6, 2017; 14 pages.
Office Action received in U.S. Appl. No. 11/084,350 dated Jul. 10, 2008; 15 pages.

* cited by examiner

LAMINOUS VASCULAR CONSTRUCTS COMBINING CELL SHEET ENGINEERING AND ELECTROSPINNING TECHNOLOGIES

CROSS-REFERENCE AND RELATED APPLICATIONS

The present application claims benefit of U.S. Provisional Patent No. 61/892,866, filed Oct. 18, 2013, the entire content of the application is hereby incorporated by reference.

U.S. GOVERNMENT RIGHTS

This invention was made with U.S. support under Grant No. W81XWH-07-1-0718 awarded by the Telemedicine and Advanced Technology Research Center (TATRC) at the U.S. Army Medical Research and Material Command (USAM-RMC). The U.S. government has certain rights in this invention.

BACKGROUND

Vascular reconstruction remains a clinical dilemma for patients requiring coronary artery bypass, peripheral vascular surgery, or arteriovenous fistula. Over 1 million procedures of coronary revascularization are performed annually in the United States. Despite their utility in the absence of autologous vessel replacement, permanent prosthetic vascular graft materials present a lifetime risk of thrombosis and infection. Alternatively, tissue engineering offers an attractive option for vascular grafting, particularly for creating small-diameter (e.g., <5 mm) blood vessels by combining patient's own cells with a natural and/or synthetic vascular scaffold to yield an implantable vascular graft.

Researchers have focused on the endothelialization of the lumen of vascular scaffolds to produce an anti-thrombogenic surface. The integrity of these endothelialized vascular scaffolds, however, has been suboptimal, both physiologically and structurally compared to native arteries.

Other types of vascular scaffolds have been proposed in which an electrospun matrix allows for endothelial cell (EC) adhesion onto the luminal surface and homogenous infiltration of smooth muscle cells (SMC) into the outer layer. See, Ju, Y. M., et al., Bilayered scaffold for engineering cellularized blood vessels, Biomaterials, 2010; 31(15):4313-21. However, uniform and effective cell seeding is challenging when an electrospun matrix alone serves as the vascular scaffold.

In practice, it is difficult to achieve the architecture of an outer smooth muscle cell layer in a vascular construct using convention smooth muscle cell seeding techniques. Accordingly, there exists a need for methods of fabricating mature smooth muscle layers in vascular constructs.

SUMMARY OF THE INVENTION

Engineered vascular grafts and scaffolds, described herein, mimic native blood vessels by combining autologous vascular cells, e.g., endothelial cells (EC) or smooth muscle cells (SMC), with a tubular scaffold under suitable culture conditions, resulting in a cellularized vascular scaffold that can be implanted in vivo. Smooth muscle cells in particular can play important roles by supporting structure and providing contractile function in several body structures, for example, in blood vessels, gastrointestinal tract, bladder and respiratory tract. Coating the lumen of synthetic vascular scaffolds with endothelial cells has been shown to prevent acute thrombosis. In addition, cell-to-cell communication between endothelial cells and smooth muscle cells is important for long-term patency by modulating the behavior and function of blood vessels.

Laminous vascular scaffolds and methods of fabricating the same are disclosed herein. By combining electrospun matrices with cell sheet technologies, vascular constructs with one or more mature smooth muscle layers can be obtained for reconstruction of blood vessels, heart valves and the like. An engineered cell sheet, wrapped around an electrospun vascular scaffold, provided a mature smooth muscle cell (SMC) layer that expressed strong cell-to-cell junction markers and contractile proteins. Preconditioning the cell sheet covered, vascular scaffold in a bioreactor system maintained cell viability and infiltration into the scaffold.

In certain embodiments, cell sheet engineering has been developed using a temperature-responsive substrate to fabricate mature tissue layers in vitro. This technology permits preservation of cell-to-cell junction proteins, as well as extracellular matrix (ECM), by avoiding enzymatic dissociation during manipulation. In some embodiments, the temperature-responsive culture surface is fabricated by grafting poly(N-isoproplyacrylamide) (PIPAAm), a temperature-responsive polymer, onto a conventional tissue culture dish. At 37° C., the surface becomes hydrophobic and cells can readily attach and proliferate on the surface. At 20° C., the surface of the PIPAAm-grafted dish becomes hydrophilic and the cell monolayer can be detached from the surface. Therefore, the cultured confluent cells are easily harvested as an intact cell sheet by decreasing the temperature to yield matured tissue constructs.

The vascular scaffolds, disclosed herein, can comprise a durable biomaterial that is capable of withstanding physiological hemodynamic forces while maintaining structural integrity until mature tissue forms in vivo. Also described herein are vascular scaffolds that, after cell seeding and preparation by in vitro culture, maintain standards such as high burst pressure strength, resistance to material fatigue, ease of suturing, and reliability and consistency of manufacture.

In some embodiments, the vascular scaffolds are produced using electrospinning technology. Electrospinning uses high-voltage electrostatic fields to generate nano- to micro-scale fibers, provides a biomimetic environment designed to resemble the ECM of native vasculature. An electrospun vascular scaffold that allows for endothelial cell adhesion onto the luminal surface and homogenous infiltration of smooth muscle cells into the porous outer layer is described herein. In some embodiments, the electrospun vascular scaffold is biodegradable, biologically and biomechanically stable, and is able to support vascular cell accommodation. Moreover, the electrospun vascular scaffold can be produced in various dimensions with consistency in composition and physical properties. The resulting electrospun vascular scaffold provides adequate biomechanical properties that withstand physiologically relevant vascular conditions.

Also described herein is a (e.g., one or more) prefabricated smooth muscle cell sheet combined with an electrospun vascular scaffold. The cell sheet provided enhanced cell seeding efficiency as well as completely preserving junctional and extracellular matrix proteins by combining with the electrospun vascular scaffold. In another embodiment, one or more cell sheets combined with an electrospun vascular scaffold is preconditioned in a bioreactor. Cell (e.g., smooth muscle cell) viability and phenotypic expression during the pulsatile bioreactor preconditioning to overcome the diffusion limitation of multilayered cell sheets was assessed as described herein.

In one embodiment, the invention relates to a method of producing a tissue engineered vascular construct. The method comprises forming an electrospun biocompatible matrix in a tubular configuration, culturing a cell population comprising smooth muscle cells to form a cell sheet and applying the cell sheet to the outside of the matrix to form a vascular construct.

In another embodiment of the method of producing a tissue engineered vascular construct, at least two cell sheets (e.g., 2, 3, 4, 5, 6, 7, or more cell sheets) are applied to the outside of the matrix to.

In another embodiment of the method of producing a tissue engineered vascular construct, further comprises seeding the inside of the matrix with a population of endothelial cells.

In another embodiment of the methods described herein, the tubular matrix comprises at least one natural component from about 25 percent to about 75 percent by weight. In some embodiments, the tubular matrix comprises an electrospun matrix comprising at least one natural component and at least one synthetic polymer component. For example, the natural component can comprise collagen and the synthetic polymer component can comprise poly(ε-caprolactone) (PCL).

In another embodiment, the method of producing a tissue engineered vascular construct further comprises attaching a first end and a second end of the vascular construct to a first attachment and a second attachment element in a preconditioning chamber, wherein the first attachment and the second attachment elements each have a channel that is fluidly coupled to a fluid flow system. The method further comprises preconditioning the construct with the flow system by moving a biological fluid through the construct, wherein a flow-rate and a pulse-rate of the biological fluid is controlled such that a preconditioned vascular construct is produced.

In another embodiment, the step of preconditioning the construct comprises moving the biological fluid through an inside surface of the seeded tubular matrix in a closed fluid flow system.

In another embodiment, the step of preconditioning the seeded tubular matrix further comprises moving a biological fluid having a composition and viscosity that mimics blood through the inside surface of the attached matrix as a pulsed flow to induce a wall shear stress of at least 10 dynes/cm$^2$ so that the vascular construct is exposed to fluid flow conditions that mimic flow of blood through a native blood vessel.

In yet another embodiment, the method of producing a tissue engineered vascular construct further comprises continuing exposure of the cells on the inside surface of the matrix to the pulsed fluid flow to allow the seeded cells to develop under fluid flow conditions until the matrix can withstand a wall pressure distribution of at least 60 mmHg.

In some embodiments, the pulsed flow has a pulse-rate that is varied over time to induce a wall shear stress in the range of about 10 dynes/cm$^2$ to about 45 dynes$^2$. In other embodiments, the pulsed flow has a pulse-rate that is varied over time to induce a wall pressure distribution in the range of about 60 mmHg to about 200 mmHg.

In some embodiments, the biological fluid is moved through the seeded tubular matrix by a pump.

In some embodiments, the smooth muscle cells are derived from progenitor cells isolated from peripheral blood or bone marrow.

In another embodiment, the invention relates to a tissue engineered vascular construct. The tissue engineered vascular construct comprises an electrospun biocompatible matrix in a tubular configuration and a population of smooth muscle cells cultured to form one or more cell sheets, the one or more cell sheets applied to the outside of the matrix to form a vascular construct.

In some embodiments, the vascular construct comprises at least 2 cell sheets (e.g., 2, 3, 4, 5, 6, 7, or more cell sheets) that are applied to the outside of the matrix.

In some embodiments, the vascular construct further comprises a population of endothelial cells seeding onto the inside the tubular matrix.

In some embodiments of the vascular construct, the tubular matrix comprises at least one natural component from about 25 percent to about 75 percent by weight. In another embodiment, the tubular matrix comprises an electrospun matrix comprising at least one natural component and at least one synthetic polymer component. For example, the natural component can comprise collagen and the synthetic polymer component can comprise poly(ε-caprolactone) (PCL).

In some embodiments of the vascular construct, the smooth muscle cells are derived from progenitor cells isolated from peripheral blood or bone marrow. In some embodiments, the population of smooth muscle cells are cultured into one or more patterns.

In another embodiment, the vascular construct further comprises a population of endothelial cells, applied to the inside of the matrix.

BRIEF DESCRIPTION OF DRAWINGS

FIG. 1A is a photograph of the electrospun matrix component of a laminous scaffold, according to one embodiment of the invention.

FIG. 1B is scanning electron microscope (SEM) image of the electronspun matrix of FIG. 1A.

FIG. 1C is a photograph of a SMC cell sheet component of a laminous scaffold, according to one embodiment of the invention.

FIG. 1D is a photograph of the cell sheet of FIG. 1C being wrapped around the electrospun matrix of FIG. 1A.

FIGS. 2A and 2B provides micrographs illustrating DAPI (FIG. 2A) and TUNEL (FIG. 2B) staining of manual seeded matrices versus cell sheet/electrospun laminous scaffolds at 1 day after seeding.

FIG. 2C is a graph providing quantitative data of cell seeding efficiency.

FIG. 2D is a graph showing the percentage of apoptotic cells (TUNEL positive nuclei) after cell seeding by manual seeding or cell sheet methods (n=3, *P<0.05).

FIG. 3A shows micrographs of the walls of a cellularized vascular scaffolds according to one embodiment of the invention. Immunofluorescent staining of cellularized vascular scaffolds for α-SMA, connexin 43 (CX43) and MLCK is shown for a manual seeded construct (upper) and a smooth muscle cell sheet construct (bottom) after 5-day cell culture.

FIG. 3B shows the Western Blot for the cell-seeded and vascular scaffolds by manual seeding and cell sheet methods.

FIG. 3C provides analysis of the Western blot shown in FIG. 3B for the cell-seeded and vascular scaffolds by manual seeding and cell sheet methods.

FIG. 4A and FIG. 4B provides DAPI staining (FIG. 4A) and TUNEL staining (FIG. 4B), respectively, of the cell sheet-scaffolds at 5 days after static culture (upper panels) and preconditioning by pulsatile bioreactor (bottom panels).

FIG. 4C is a graph of the percentage of TUNEL positive nuclei quantified by total nuclei (n=3, *P<0.05).

FIG. 5A shows immunofluorescent staining of the cell sheet-vascular scaffolds.

FIG. 5B shows the Western Blot for the cell sheet-vascular scaffolds.

FIG. 5C provides quantitative data from the Western Blot in FIG. 5B for the cell sheet-vascular scaffolds (n=3, *P<0.05).

FIG. 6A provides stress-strain curves for the three alternative structures (scaffold, manually seeded, and cell sheet wrapped).

FIG. 6B is a graph of ultimate tensile strength for the scaffold, manually seeded, and cell sheet wrapped structures.

FIG. 6C is a graph of Young's modulus for the scaffold, manually seeded, and cell sheet wrapped structures.

FIG. 6D is a graph illustrating elongation at break of the scaffold, manually seeded, and cell sheet wrapped vascular scaffolds (n=3, *P<0.05).

DETAILED DESCRIPTION

Figures 1A, 1B, 1C, 1D:
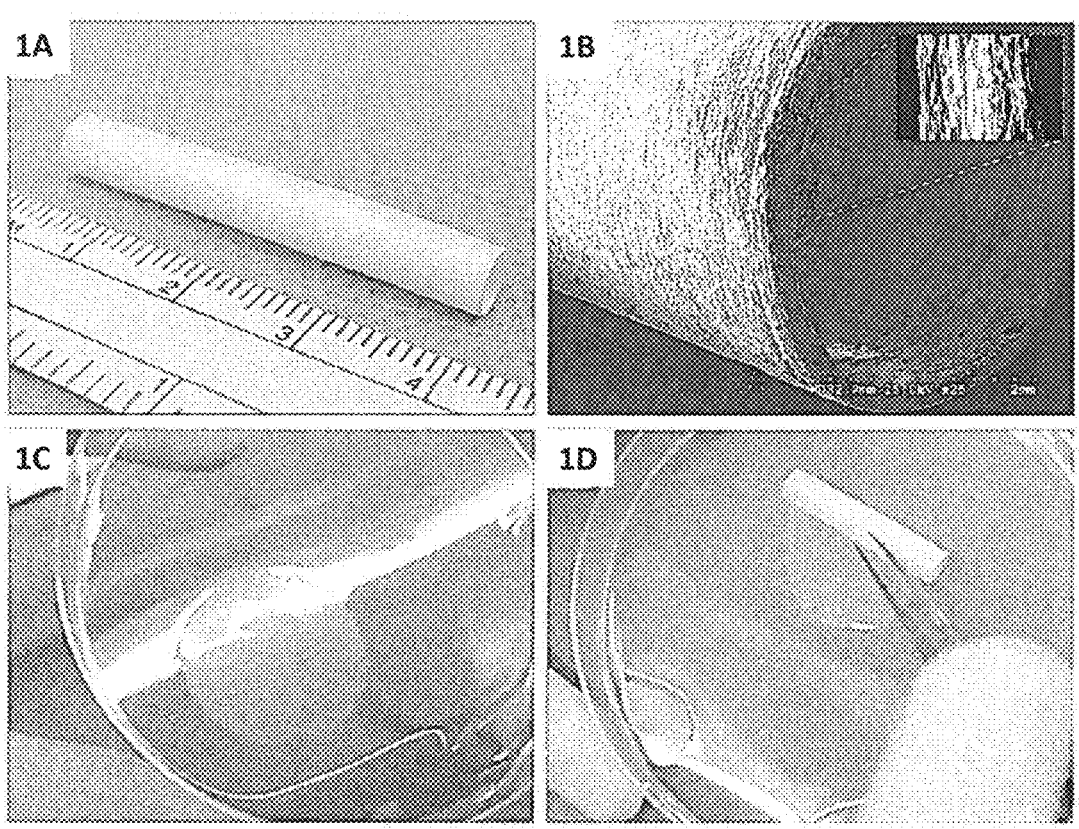
FIGS. 1A-1D illustrate the construction of laminous scaffolds according to an embodiment of the invention.

As used herein, the terms "electrospinning" or "electrospun," refers to any method where materials are streamed, sprayed, sputtered, dripped, or otherwise transported in the presence of an electric field. The electrospun material can be deposited from the direction of a charged container towards a grounded target, or from a grounded container in the direction of a charged target. In particular, the term "electrospinning" means a process in which fibers are formed from a charged solution comprising at least one natural biological material, at least one synthetic polymer material, or a combination thereof by streaming the electrically charged solution through an opening or orifice towards a grounded target.

Electrospinning allows flexibility and customization of a construct to virtually any shape. In some embodiments of the present invention, the shape of an electrospun matrix is tubular or substantially tubular. In other embodiments, the shape of the electrospun matrix is planar, semi-circular, oval, or hourglass shaped.

In some embodiments, the electrospun matrix comprises a natural polymer. In one embodiment, the natural compound comprises collagen or fibrous collagen. For example, different types of collagen include, but are not limited to collagen I, collagen II, collagen III, collagen IV, collagen V, collagen VI, collagen VII, collagen VIII, collagen IX, and collagen X. In another embodiment, the natural compound comprises elastin. Elastin fibers are responsible for the elastic properties of several tissues. Elastin is found, for example, in skin, blood vessels, and tissues of the lung where it imparts strength, elasticity and flexibility. In another embodiment, the natural compound comprises collagen and elastin. Other natural polymers include, but is not limited to, hyaluronan, chondroitin sulfate, dermatan sulfate, keratan sulfate, heparan sulfate, and heparin.

In some embodiments, the electrospun vascular matrix comprises a synthetic polymer. In one embodiment, the synthetic polymer comprises a biocompatible synthetic polymer. In one embodiment, the synthetic polymer comprises poly(ε-caprolactone) (PCL). Other synthetic polymers include, but are not limited to, poly(amino acids), polyhydroxybutyrate (PHB), poly(3-hydroxybutyric acid-co-3-hydroxyvaleric acid) (PHBV), polyphosphazenes, polypropylene fumarate), poly(urethanes), poly(siloxanes) or silicones, poly(ethylene), poly(vinyl pyrrolidone), poly (2-hydroxy ethyl methacrylate), poly(N-vinyl pyrrolidone), poly(methyl methacrylate), poly(vinyl alcohol) (PVA), poly (acrylic acid), poly(vinyl acetate), polyacrylamide, poly (ethylene-co-vinyl acetate), poly(ethylene glycol), poly (methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO) and polyorthoesters or any other similar synthetic polymers that may be developed that are biologically compatible. In certain embodiments, the synthetic polymer is also biodegradable.

In another embodiment, the electrospun vascular matrix comprises a composite of at least one (e.g., one or more) natural polymer and at least one (e.g., one or more) synthetic polymer. For example, the electrospun vascular matrix comprises a composite of collagen and PCL. In another embodiment, the electrospun vascular matrix comprises a composite of collagen, elastin and PCL. In another embodiment, the electrospun vascular matrix comprises a composite of elastin and PCL. The vascular matrix can comprise any of the natural and synthetic polymers described herein. In some embodiments, the at least one natural polymer comprises collagen and elastin. In some embodiments, collagen comprises a higher weight percentage than elastin. For example, collagen can comprise greater than 40 percent of the natural material component. In other embodiments, a ratio of collagen and PCL can be altered and tailored to fit the specific application. For example, levels of collagen and elastin can vary from the more elastic vessels closer to the heart to less compliant (elastic) vessels further from the heart. A vessel such as the aorta would have a greater elastin content than, for example, a distal vessel. The percentages of collagen (e.g., collagen I, collagen III) and elastin, can be whatever is desired, as long as the molecular weight of these collagens is sufficient to form fibers in the electrospinning process. For example, collagen III can be used in for vascular applications, such as blood vessels and collagen II, for instance, used for cartilage applications. In some embodiments, ratios of collagen I can comprise about 25% to about 75%, about 40% to about 80%, or about 50% to about 100%. In other embodiments, elastin can be used in ratios from about 5% to about 50%. In other embodiments, PLGA or another synthetic biodegradable polymers can be used in ratios from about 5% to about 80%. In another embodiment, no synthetic polymers are used and the vascular matrix comprises natural or biological polymers, e.g., for a completely biological substrate.

In some embodiments of an electrospun vascular matrix comprising a natural polymer, the natural polymer comprising from about 5 percent to about 95 percent by weight of the electrospun vascular matrix. In some embodiments, the natural polymer comprises about 25 percent to about 75 percent by weight.

In some embodiments of an electrospun vascular matrix comprising a synthetic polymer, the synthetic polymer comprising from about 5 percent to about 95 percent by weight of the electrospun vascular matrix. In some embodiments, the synthetic polymer comprises about 25 percent to about 75 percent by weight.

The electrospun polymers and compounds described herein can comprise any concentration that allows for electrospinning. In one embodiment, the polymers and compounds can be present in the solution at concentrations between about 0 and about 1.000 g/ml. In another embodiment, the compounds can be present in the solution at concentrations between 10-15 w/v % (100-150 mg/ml or 0-0.1 g/L). The terms "solution" and "solvent" is used in the context of producing an electrospun matrix and describes a liquid that is capable of being charged and which comprises at least one natural material, at least one synthetic material, or a combination thereof. In a preferred embodiment, the fluid comprises at least one type of collagen, an additional natural material such as at least one type of elastin and at least one synthetic polymer, e.g., poly-L glycolic acid (PLGA). In some embodiments, the compounds and polymers described herein can be dissolved in any solvent that allows delivery of the compound to the orifice, tip of a syringe, under conditions that the compound is electrospun. For example, any number of solvents can be used for dissolving or suspending a material or a substance. Electrospinning techniques often require specific solvent conditions. For example, collagen can be electrodeposited as a solution or suspension in water, 2,2,2-trifluoroethanol, 1,1,1,3,3,3-hexafluoro-2-propanol (also known as hexafluoroisopropanol or HFIP or HFP), or combinations thereof. By way of another example, fibrin monomer can be electrodeposited or electrospun from solvents such as urea, monochloroacetic acid, water, 2,2,2-trifluoroethanol, HFIP, or combinations thereof. In another example, elastin can be electrodeposited as a solution or suspension in water, 2,2,2-trifluoroethanol, isopropanol, HFIP, or combinations thereof, such as isopropanol and water. In one embodiment, elastin is electrospun from a solution of 70% isopropanol and 30% water containing 250 mg/ml of elastin. In other embodiments, other lower order alcohols, especially halogenated alcohols, are used. For example, other solvents that can be used or combined with other solvents in electrospinning natural matrix materials include, but is not limited to, acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone. Organic solvents such as methanol, chloroform, and trifluoroethanol (TFE) and emulsifying agents.

By varying the composition of the fibers being electrospun, it can be appreciated by one of ordinary skill in the art that fibers having different physical or chemical properties can be obtained. By way of example, in one embodiment, a liquid containing a plurality of components can be spun, each component contributing a desired characteristic to the finished product (e.g. tubular matrix). In another embodiment, fibers of different compositions from multiple liquid sources (e.g., one or more solutions) can be simultaneously spun, and can be simultaneously deposited to form a matrix (e.g. tubular matrix). In this embodiment, the resulting matrix comprises a plurality of layers of intermingled fibers of the different compounds. This plurality of layers of the different compounds can convey a desired characteristic in the resulting composite matrix. For example, one layer of the electrospun matrix can contribute to elastic properties. Also, another layer can contribute to the mechanical strength of the composite matrix. The methods described herein can be used to create electrospun constructs or scaffolds comprising multiple layers (e.g., vascular constructs).

In some embodiments, the electrospun matrix comprises an ultrastructure with a three-dimensional network that can support cell growth, proliferation, differentiation and development. The spatial distance between the fibers plays an important role in cells being able to obtain nutrients for growth as well as for allowing cell-cell interactions to occur. In the methods described herein, the pore size in an electrospun matrix can be controlled through manipulation of the composition of the material and the parameters of electrospinning. In some embodiments, the electrospun matrix has a pore size that is large enough for cell infiltration. In various embodiments of the invention, the distance between the fibers can be about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 2 microns, 5 microns, 10 microns, 10 microns, 50 microns, about 100 microns, about 150 microns, about 200 microns, about 250 microns, about 300 microns, about 350 microns, about 400 microns, about 450 microns, or about 500 microns. In various embodiments the distance between the fibers may be less than 50 nanometers or greater than 500 microns and any length between the quoted ranges as well as integers.

Additionally, in various embodiments of the invention, the fibers can have a diameter of about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 50 microns, about 100 microns, about 150 microns, about 200 microns, about 250 microns, about 300 microns, about 350 microns, about 400 microns, about 450 microns, or about 500 microns, or the diameter may be less than 50 nanometers or greater than 500 microns and any diameter between the quoted ranges as well as integers.

In one embodiment, the average pore diameter is about 500 nanometers or less (e.g., 500 nm, 400 nm, 300 nm, 200 nm, 100 nm, or less than 100 nm). In another embodiment, the average pore diameter is about 1 micron (μm) or less. In another embodiment, the average pore diameter is about 2 microns or less. In another embodiment, the average pore diameter is about 1 micro to about 2 microns. In another embodiment, the average pore diameter is greater than 1 micron. In yet another embodiment, the average pore diameter is greater than 2 microns. One of ordinary skill in the art can readily appreciate that the average pore diameter can depend on the size, type, or source of the cell(s) being used to seed the matrix. Larger sized cells can generally require larger sized pores for adequate growth, proliferation, differentiation and development. Smaller cells can be grown on a matrix having smaller pore diameters.

The pore size of an electrospun matrix can be readily manipulated through control of process parameters, for example by controlling fiber deposition rate through electric field strength and mandrel motion, by varying solution concentration (and thus fiber size). Porosity can also be manipulated by mixing porogenic materials, such as salts or other extractable agents, the dissolution of which will leave holes of defined sizes in the matrix. The pore size can also be controlled by the amount of cross-linking present in the matrix.

Another aspect of the invention described herein relates to cell sheets. A cell sheet comprises at least one type of cell (e.g., a smooth muscle cell) cultured on a thermo-sensitive poly(N-isoproplyacrylamide) (PIPAAm) coated culture dish. The at least one type of cell is grown to confluence at appropriate culture conditions. Confluent cells can be recovered as an intact sheet by reducing the temperature. For example, cells can be cultured at about 37° C. Reducing the temperature to about 20° C. detaches the cell as an intact sheet from the culture dish. One of ordinary skill in the art can readily appreciate other thermo-sensitive polymers that can be used to creating and forming suitable cell sheets as described herein.

In one embodiment, the cell sheet comprises at least one type of cell. In another embodiment, the cell sheet comprises a plurality of different cells. In yet another embodiment, the cell sheet comprises 2, 3, 4, or 5 types of cells. For example, any one of smooth muscle cells (e.g., vascular smooth muscle cells), embryonic stem cells (ESC), bone marrow stem cells, mesenchymal stem cells (MSC), and any other totipotent, pluripotent or multipotent stem cells that can form or differentiate into smooth muscle cells can be used in the cell sheets described herein. In another embodiment, endothelial cells (e.g., vascular endothelial cells), fibroblasts, or any other cell type in vascular tissue can comprise a cell sheet. As used herein, "smooth muscle cell" includes any progenitor cell that can differentiate into a smooth muscle cell. As used herein, "endothelial cell" includes any progenitor cell that can differentiate into an endothelial cell.

Cell types include, but are not limited to, endothelial cells such as human endothelial cells, progenitor cells isolated from the peripheral blood bone that can be induced to differentiate into different cells, stem cells, committed stem cells, and/or differentiated cells may be used. Also, depending on the type of tissue or organ being made, specific types of committed stem cells can be used. For instance, myoblast cells can be used to build various muscle structures. Other types of committed stem cells can be used to make organs or organ-like tissue such as heart, kidney, liver, pancreas, spleen, bladder, ureter and urethra. Other cells include, but are not limited to, endothelial cells, muscle cells, smooth muscle cells, fibroblasts, osteoblasts, myoblasts, neuroblasts, fibroblasts, glioblasts; germ cells, hepatocytes, chondrocytes, keratinocytes, cardiac muscle cells, connective tissue cells, epithelial cells, endothelial cells, hormone-secreting cells, cells of the immune system, neurons, cells from the heart, kidney, liver, pancreas, spleen, bladder, ureter and urethra, and the like. In some embodiments it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the biochemical environment of the liver.

The cell sheets used in methods and constructs described herein can comprise isolated primary smooth muscle cells or cell lines derived from such primary cells, tumors and the like. The cells used may be available smooth muscle cell lines such as internal intestinal or anal sphincter smooth muscle cell lines, airway smooth muscle cell lines and other commercially available smooth muscle cell lines. For example, cell lines derived from muscle may be obtained from a cell line depository such as the American Type Culture Collection (ATCC, Bethesda, Md.). Such cell smooth muscle cell lines include human iliac vein smooth muscle cells (HIVS-125; ATCC accession no. CRL-2482), Syrian Golden Hamster ductus deferens smooth muscle cells (DDT1; CRL-1701), human umbical vein smooth muscle cells (HUVS-112D: CRL-2481), rat aorta smooth muscle cells (Hep-Sa; CRL-2018), and human aortic smooth muscle cells (T/G HA-VSMC; CRL-2498). The conditions for growth of the specific cell line purchased will depend on the biological source and generally instructions for the growth of the cells are made available along with the cell lines from ATCC. In other applications, the smooth muscle cells can be obtained from the patient who will be the recipient of the tissue engineering structure. Such autologous cells can be obtained from a surgical excision or a biopsy and can be isolated, cultured, expanded or enriched according to various techniques known in the art.

In one aspect, the cell sheets comprise isolated cells or cell lines. The isolated cells or cell lines can be pluripotent (obtained by isolation or enrichment or induced dedifferentiation) and able to differentiate into cells that possess contractile function. The cells may be derived from any vertebrate or non-vertebrate animal source. For example, the animal source may be human, monkey or other primate, mouse, rat, rabbit, cat, dog, goat, sheep, pig, horse, cow, fish, bird or any other animal from which such cells 30 may be harvested. In one aspect, the smooth muscle cells used in the three-dimensional culture are mammalian cells. In another aspect, the cells are human or primate cells, but rat and rabbit cells also will be usefully employed herein. The appropriate growth factors may be added to the culture. The concentration of such factors maintained in the cultures can be monitored and adjusted to optimize growth. Cells cultured in this manner can be used for transplantation or implantation in vivo. As noted above, it will often be preferable to obtain the muscle cells from the patient's own tissues (autologous cells).

The methods and constructs described herein can comprise primary smooth muscle cells isolated from a 5 variety of organs which contain circular smooth muscle. Organs that contain circular smooth muscle include the esophagus, stomach, duodenum, jejumen, ileum, colon, trachea, bronchial tubes, uterus, blood vessels, lymphatic vessels, urethra, glandular ducts, and the ciliary muscle of the eye. For example, smooth muscle cells can be isolated from the internal anal sphincter (IAS) of New Zealand White rabbits as described previously (Bitar et al., Am J Physiol 260: G537-10 G542, 1991; Bitar et al., Am J Physiol 242: G400-G407, 1982).

In another embodiment, at least one cell sheet can be rolled, wrapped, or layered around (e.g., exterior surface) an electrospun scaffold. In other embodiments, 2, 3, 4, 5, 6, 7, 8, 9, 10 or more cell sheets are rolled, wrapped, or layered around an electrospun scaffold. The number of cell sheets that are wrapped around the electrospun tubular matrix can vary. In one embodiment, the number of cell sheets wrapped around the electrospun matrix comprises approximately the number of cell sheets needed to achieve a desired thickness of cells on the matrix. For example, about 3 cell sheets of smooth muscle cells can be wrapped around an electrospun matrix to achieve approximately the thickness of smooth muscle cells in a native vascular tissue.

In another embodiment, at least one cell sheet can be rolled, placed, or layered on the lumen (e.g., interior surface) of an electrospun scaffold. In other embodiments, 2, 3, 4, 5, 6, 7, 8, 9, 10 or more cell sheets are rolled, placed, or layered on the lumen of an electrospun scaffold. The number of cell sheets that are placed on the lumen of the electrospun matrix can vary. In one embodiment, the number of cell sheets placed on the lumen of the electrospun matrix comprises approximately the number the number of cell sheets needed to achieve a desired thickness of cells in the lumen of the matrix. For example, about 1 cell sheet of endothelial cells can be placed in the lumen of the electrospun matrix to achieve approximately the thickness of vascular endothelial cells in a native blood vessel.

In another embodiment, the cell sheets described herein can be prepared so one or more cell types comprising the cell sheet are grown in a (one or more) patterned or otherwise ordered geometry (e.g., spatial orientation). For example, in some embodiments, lithography can be used to direct the growth, alignment and/or spatial orientation of the cells. In one embodiment, a cell sheet comprises smooth muscle cells. The smooth muscle cells are substantially aligned (e.g., axially, longitudinally). The cell sheet comprising the substantially aligned smooth muscle cells can be wrapped around an electrospun tubular matrix. The resulting tubular matrix wrapped with the cell sheet comprises cells aligned and/or have a similar spatial orientation. One of ordinary skill in the art will readily appreciate that the cellular spatial orientation of the cell sheet and wrapping the aligned cells on the matrix can be adjusted. Placement of the cell sheets on the matrix can allow for mimicking physiological and/or native conditions, for example, in a blood vessel.

In another embodiment, one or more templates can be used to culture one or more cell types in a patterned or otherwise ordered geometry. For example, a population of cells (e.g., one or more cell types) can grow in a pattern defined by the PIPAAm coated culture dish, as described herein. The width or diameter of the pattern, for example, can be about 200 nm to about 10 µm. In another embodiment, the pattern width is about 500 nm to about 5 µm. In another embodiment, the pattern width is about 1 µm to about 3 µm. One of skill in the art will readily appreciate that the pattern width can influence the growth and spacing of the cells.

Another aspect of the invention described herein relates to seeding the lumen (interior surface) of the electrospun tubular matrix. In some embodiments, the seeding of the lumen with cells comprises manually seeding the lumen. For example, in one embodiment manually seeding the matrix can comprise pipetting cells onto the luminal surface of the matrix. Pipetting cells onto the luminal surface can comprise adding cells to a portion of the lumen. After some period of time (e.g., 1 min, 2 min, 5 min, 10 min, 20 min, 30 min, 45 min, 60 min, 90 min, 2 hrs, 3 hrs, 4 hrs, 6 hrs, 12 hrs, etc.), the matrix is rotated and additional cells are added to a different portion of the lumen. This can be repeated until the entire lumen is seeded with cells. Rotation of the matrix can be, for example, about 10 degrees, about 20, about 30, about 40, about 50, about 60, about 70, about 80, or about 90 degrees. One of skill in the art will appreciate that the degree of rotation of the matrix can vary as long as the lumen of the matrix is substantially seeded with cells. In another embodiment, manually seeding the matrix comprises providing a solution comprising a population of cells to the lumen of the electrospun matrix. The population of cells can comprise one or more different cell types. For example, the cells comprise endothelial cells. It will be appreciated by one of ordinary skill in the art that other methods can be employed to manually seed the lumen of the electrospun matrix.

In one embodiment, seeding the lumen of the electrospun matrix comprises one or more types of cells. For example, the lumen of the electrospun matrix is seeded with solution comprising endothelial cells, endothelial progenitor cells, stem cells or combinations thereof.

Another aspect of the invention, as described herein, is directed to a bioreactor system. The bioreactor system, described in detail below, can be used for vascular applications, including for example, preconditioning the electrospun tubular matrix comprising one or more cell sheets. For example, the bioreactor system can generate and record physiologic flow and pressure. The system can also generate mechanical stress. The system can also provide an external flow of cell culture media or any other solution. The system can also maintain any one or more of the following: gases, nutrients, temperature, sterility and other conditions.

The term "bioreactor system" as used herein refers to a system that allows a matrix seeded with cells to be conditioned such that the cells on the matrix develop under physiological conditions. For example, to create blood vessels, a matrix can be seeded with endothelial cells and the endothelial cells allowed to develop under native fluid conditions such as pulsed conditions that mimic the pulse rate of blood through native vessels, or fluid flow conditions with alterations in pressure. To begin with, the pulse rate and the flow rate can be slow until the cells adjust to this pulse-rate or flow-rate, the flow-rate and pulse-rate can then gradually be increased until the cells adjust to the new pulse-rate and flow-rate and so forth. By gradually increasing the pulse-rate and the flow-rate, the vessels become conditioned to being able to withstand pressure as high as those produced during each heartbeat.

In one embodiment, a biological fluid (e.g., culture media) can be moved through the inside surface of the attached matrix (lumen) as a continuous flow, for example at a flow-rate that can be incremented over time to induce a wall shear in the range of about 0 dyne/cm$^2$ to about 100 dynes/cm$^2$. In some embodiments, the wall shear is about 1, about 5, about 10, about 20, about 30, about 40, about 50, about 60, about 70, about 80, about 90, or about 100 dynes/cm$^2$.

In another embodiment, the step of preconditioning the matrix can involve moving the biological fluid through the inside surface of the attached matrix as a pulsed flow, for example, a pulsed flow that has a pulse-rate which is incremented over time to induce a wall shear in the range of about 1 dynes/cm$^2$ to about 75 dynes/cm$^2$. In some embodiments, the wall shear is about 1, about 5, about 10, about 20, about 30, about 40, about 50, about 60, about 70, or about 75 dynes/cm². The pulse-rate can be incremented over time to induce a wall pressure distribution in the engineered blood vessel in the range of about 50 to about 250 mmHg. A different of the same biological fluid can also be used to precondition the outside of the matrix.

The term "biological fluid" or "culture media" as used herein refers a liquid that can be used to precondition an engineered blood vessel. The biological fluid has a composition and viscosity that mimics blood so that the engineered blood vessels are exposed to the same fluid flow dynamics as native blood vessels. Examples of biological fluids can include any buffer, cell culture medium, or medium of physiological fluid (e.g., DMEM with 10% FCS with a blood viscosity). The viscosity of the fluids can be altered by adding high molecular weight proteins such as 100 kDa dextran. Other molecular weight dextrans can also be used. It will be appreciated that the amount of dextran to be used depends on the molecular weight and can range from about 10%, 20%, 30%, 40%, 50%, and 60%. The composition may also be varied by adding other blood like constituents such as salts For example, any one of a number of commercially available cell culture mediums can be used in the bioreactor system described herein. Type of cell culture media include for example, but is not limited to, endothelial cell media, smooth muscle cell media, DMEM, EGM-2, RPMI 1640, MEM, and EBM (endothelial basal medium).

In one embodiment, a bioreactor system preconditions an electrospun matrix that was previously seeded with one or more cell sheets and/or manually seeded with cells. In another embodiment, a bioreactor system preconditions an electrospun matrix that was previously seeded with one or more cell sheets. In another embodiment, a bioreactor system preconditions an electrospun matrix that was previously manually seeded with cells. It will be apparent to one of ordinary skill in the art that preconditioning of the matrix can be performed after all or some of the cells sheets and/or manual seeding is completed. In other embodiments, the electrospun matrix can be preconditioned after each cell sheet layer is wrapped around the matrix.

EXAMPLES

Example 1

Tissue engineering is an approach to create functional small-diameter (<5 mm) blood vessels by combining autologous cells with a natural and/or synthetic scaffold under suitable culture conditions, resulting in a tubular construct that can be implanted in vivo. A vascular scaffold was fabricated by electrospinning poly(ε-caprolactone) (PCL) and type I collagen that mimics the structural and biomechanical properties of native vessels. In this study, a smooth muscle cell (SMC) sheet was combined with the electrospun vascular scaffolds to produce a more mature smooth muscle layer as compared to the conventional cell seeding method. The pre-fabricated SMC sheet, wrapped around the vascular scaffold, provided a mature smooth muscle layer that expressed strong cell-to-cell junction and contractile proteins. Moreover, bioreactor-associated preconditioning of the SMC sheet-combined vascular scaffold maintained high cell viability and phenotypes, as well as cellular infiltration into the scaffold.

Fabrication of Electrospun Vascular Scaffolds

Vascular scaffolds were fabricated by electrospinning a polymer blend of poly(ε-caprolactone) (PCL) and collagen type 1. The scaffolds were electrospun using a 1:1 (weight ratio) polymer blend of PCL (Inherence viscosity=1.77 dL/g, Lactel Absorbable Polymers, Pelham, Ala., USA) and pepsin-treated type I collagen derived from calf skin (Elastin Products Co., Owensville, Mo., USA) in 1,1,1,3,3,3-hexafluoro-2-propanol (HFP). The electrospinning apparatus included a syringe pump, a high-voltage supply, and a rotating mandrel. A positive voltage (20 kV) was applied to the polymer solution by the power supply (Spellman high Voltage, Hauppauge, N.Y., USA). Two milliliter of 18% (w/v) PCL/collagen blend solution was delivered through an 18-gauge blunt tip syringe needle at a constant flow rate of 10 mL/h using a syringe pump. The collecting mandrel consisted of a 303 stainless steel rod (4.75 mm diameter). The distance between the syringe tip and the mandrel was 15 cm, and the rotation rate was approximately 5000 rpm. The electrospun scaffolds were cross-linked in the vapor of a 2.5% glutaraldehyde solution at room temperature for 8 hours. All chemical reagents were obtained from Sigma Chemical Co. (St. Louis, Mo., USA), unless stated otherwise.

The morphology of the electrospun scaffold was observed under scanning electron microscopy (SEM; Model S-2260N, Hitachi Co. Ltd., Tokyo, Japan). The electrospun scaffolds were sputter-coated with gold (Hummer™ 6.2, Anatech Ltd, Denver, N.C., USA) to a thickness of 10-15 nm. Images were acquired using an environmental SEM operating at an accelerating voltage of 25 kV with a 15 cm working distance. The SEM images were analyzed with the UTHSCSA ImageTool 3.0 (Freeware provided by the University of Texas Health Sciences Center at San Antonio, Tex., USA) to determine morphology of the scaffold.

Isolation and Culture of Primary Ovine Smooth Muscle Cells

Vascular smooth muscle cells (SMCs) were isolated from biopsies of the femoral artery of sheep (female Dorper cross, aged 3-4 months, Mocksville, N.C., USA). A femoral artery segment (3 cm length) was washed with phosphate-buffered saline (PBS) containing 1% antibiotics/antimycotics and cut longitudinally. The medial layer was obtained by gently scraping both endothelial and adventitial layers with a scalpel blade. The medial layer containing SMCs was cut (1 mm²) and placed into the tissue culture dish. To ensure SMC migration, the explants were given a small amount of medium for the first 24 hours of culture. SMCs were radially grown from the explants within 2-3 weeks of culture, and medium was exchanged every 3 days. The SMCs were cultured with smooth muscle basal medium (SmBM™, Lonza, Basel, Switzerland) supplemented with SmGM™-2 SingleQuot kit, including epidermal growth factor (EGF), basic fibroblast growth factor (bFGF), insulin, fetal bovine serum (FBS), and gentamicin/amphotericin-B, Lonza). All reagents for cell culture were purchased from Life Technologies (Grand Island, N.Y., USA), unless stated otherwise.

Pre Fabrication of SMC Sheet and Combination with Electrospun Scaffolds

Thermo-sensitive poly(N-isoproplyacrylamide) (PIPAAm)-coated culture dish was purchased from Thermo Scientific (Upcell™, Nunc, Roskilde, Denmark). Cell suspension of SMCs was plated into Upcell™ culture dish at 2×10⁶ cells/cm² and cultured for 5 days at 37° C. in a humidified incubator with 5% $CO_2$. Confluent SMCs recovered as intact cell sheet by reducing temperature to 20° C. for 30 min. To combine the SMC sheet and electrospun vascular scaffold, the prepared cell sheet was wrapped around the scaffold (3 cm length and 4.75 mm diameter) (see FIGS. 1A-1B) and incubated at 37° C., 5% $CO_2$ for 30 min. This procedure was repeated three times to prepare three-layered cell sheet vascular constructs.

For the control, manual cell seeding was performed with trypsin-dissociated SMCs. The dissociated single cells (1.0× $10^8$ cells/mL) were seeded on the outer layer of the scaffolds by 90-degree rotation every 15 min. The cell-seeded scaffolds in minimum culture medium were incubated at 37° C., 5% $CO_2$ for 2 h. After 2 h in culture, the culture medium was added to cover the entire scaffold.

Pulsatile Perfusion Bioreactor System

The SMC sheet-vascular scaffolds were mounted into a customized pulsatile perfusion bioreactor system. The bioreactor system was developed for vascular applications allows for (a) generation and recording of physiologic flow, pressure, and stretch; (b) an external flow of media; (c) maintenance of gases and nutrients in the culture medium; and (d) maintenance of temperature and sterility. Lumen flow was initiated using a computer-operated gear pump (Ismatec MCP-Z Process, Glattbrugg, Switzerland) controlled by an Ismatec ProEdit program (V1.1.00). All components were contained within the incubator and kept at 37° C., 5% $CO_2$. Mechanical stimulation using this pulsatile perfusion bioreactor was maintained by gradually increasing the lumen flow rate and shear stress. The program transitioned from steady to pulsatile flow for simulating arterial hemodynamic conditions (the vessel wall shear stress of 9.9 dyne/$cm^2$ in diastole and 13.2 dyne/$cm^2$ in systole). Pulsatile flow waveform was supplied at a frequency of 60 cycles/min. The SMC sheet-vascular scaffolds under static culture condition served as a control.

In Vitro Evaluations of the Cell Sheet-Electrospun Scaffolds

For histological evaluations, the cell-seeded scaffolds were fixed in 4% paraformaldehyde (Polyscience Inc., Warringthon Pa., USA) for 15 min and washed three times with PBS for 5 min each. Subsequently, the samples were embedded in paraffin and sectioned into 5 μm sections. To visualize the nuclei of the cell-seeded scaffolds, deparaffinized sections were stained with 4'6-diamidine-2-phenylindole (DAPI, Vector Laboratories, Burlingame, Calif., USA) one day after cell seeding and 5 days after pulsatile bioreactor, respectively.

Apoptosis was analyzed by Terminal deoxynucleotidyl Transferase (TdT)-mediated dUTP end labelling (TUNEL) staining according to manufacturer's instruction (R&D System, Minneapolis, Minn., USA). To visualize the apoptotic cells and live cells, apoptotic cells were detected using a streptavidin-horseradish peroxidase conjugate and live cells were counterstained with methyl green. TUNEL-positive cells were counted from the stained images.

Immunofluorescent Staining

To assess the maturation of vascular smooth muscle layer, immunofluorescent staining was performed using anti-α smooth muscle actin (α-SMA, Santa Cruz), anti-connexin 43 (CX43, Sigma), and myosin light chain kinase (MLCK, Epitomics, Burlingame, Calif., USA). The deparaffinized sections were permeabilized by incubation with 0.1% Triton-X 100 in PBS for 15 min, followed by incubation in serum-free protein blocker (DAKO, Glostrup, Denmark) for 15 min to reduce nonspecific background staining After a gentle rinse in PBS, the samples were incubated for 1 hour in primary antibodies (1/500 α-SMA, 1/400 CX43, and 1/200 MLCK, respectively) diluted in antibody diluent solution (DAKO). The samples were washed with PBS, and incubated with Alexa Fluor® 594 Anti-Rabbit or mouse IgG (1/200, Life Technologies) for 45 min at room temperature. Nuclei were stained using VECTASHIELD Mounting Medium with DAPI kit (Nuclear staining, Vector laboratories Inc.). The samples were visualized using a Zeiss fluorescence microscope (Carl Zeiss, Inc., Jena, Germany).

Western Blot

The cell-seeded scaffolds were homogenized in the lysis buffer (Cell Signaling Technology, Danvers, Mass., USA). Supernatants were collected by centrifugation for 10 min at 13,000 rpm, 4° C. Total protein concentration was measured by Bradford assay method using BioRad protein assay reagent (Bio-Rad Laboratories, Hercules, Calif., USA). Equal concentrations of protein were separated by 10% sodium dodecyl sulphate S4 polyacrylamide gel electrophoresis (SDS-PAGE). The protein was transferred to polyvinylidene difluoride (PVDF) membranes (Bio-Rad Inc). Membranes were blocked with 5% skim milk (BD, Franklin Lakes, N.J., USA) in TBS-T (50 mM Tris-HCl, 150 mM NaCl, pH 7.4) for 1 hour at room temperature and immunoblotted using primary antibodies to α-SMA, CX43, MLCK, and additional internal control β-actin in 5% skim milk for overnight at 4° C. The membranes were washed three times in TBS-T for 10 min and incubated with a secondary antibody (goat anti-rabbit or mouse HRP, 1:2000 dilution, Cell Signaling Technologies) prepared in TBS-T for 1 hour at room temperature and washed three times in TBS-T. The specific protein bands were detected by enhanced chemiluminescent system (Promega, Madison, Wis., USA) and the optical density was analyzed with Luminescent Image Analyzer System (LAS-3000, Fuji film Corp., Tokyo, Japan).

Tensile Testing

Tensile testing on the vascular scaffolds was performed using a uniaxial load test machine (Model #5544, Instron Corporation, Norwood, Mass., USA). Specimens from pre- and post-bioreactor conditioning were cut into a ring of 5 mm diameter for circumferential testing (n=5). The thickness of each scaffold was measured from cross-sectional SEM images. Tensile properties of the specimens were measured with a maximum 100 N load cell at a crosshead speed of 0.5 mm/s. The ultimate tensile strength, Young's modulus, and elongation at break were obtained from the stress-strain curves.

Statistical Analysis

All experiments were repeated at least three times and expressed as mean±standard deviation. Results were analyzed with Student's t-test using the Prism 5.0 software (GraphPad Software Inc., La Jolla, Calif., USA). $P<0.05$ was considered statistically significant.

Results

Combination of the Smooth Muscle Cell Sheet and Electrospun Vascular Scaffolds

The electrospinning parameters used for the fabrication of vascular scaffolds were previously optimized by controlling solution concentration, flow rate, voltage levels, rotation speed, and distance between the tip and the mandrel. The fabricated electrospun PCL/collagen scaffolds showed aligned fibrous structures with approximate diameter of 4.85±0.31 μm and pore areas of 1,102±743.93 $μm^2$ (see FIGS. 1A and 1B). To mimic the 3-D spiral organization of SMCs of native vessels, the electrospun scaffolds with fiber alignment to the circumferential direction were produced by electrospinning at high rotation rate of 5000 rpm. The electrospun vascular scaffolds had a length of 4 cm and an inner diameter of 4.75 mm with thickness of 0.3 mm.

To pre-fabricate SMC sheets by temperature changes, the cultured SMCs were grown to 100% confluency on the surface of Upcell™ culture dish. After cell seeding at 2×$10^6$ cells/$cm^2$, confluent SMC monolayer was obtained at 5 days in culture. At room temperature, SMC sheets were easily detached from the surface of the dishes, and the detached cell sheets were subsequently contracted (see FIG. 1C). For the combination of the SMC sheet and the electrospun PCL/collagen scaffold, one cell sheet was wrapped around an electrospun tubular scaffold. This procedure was repeated until triple layered cell sheets were formed (see FIG. 1D). The average thickness of a single-layered cell sheet after detachment was 43.08 μm, and the average thickness of the triple-layered cell sheet was 143.4 μm.

Cell Seeding Efficiency, Viability, and Phenotypic Expression

Figures 2A, 2B, 2C, 2D:
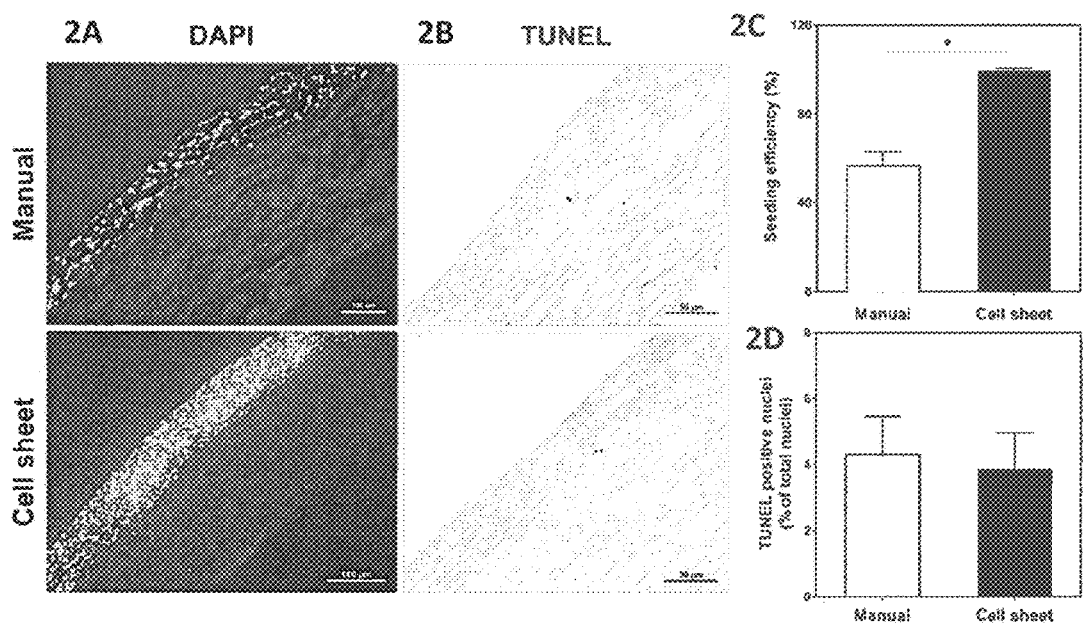
FIGS. 2A-2D illustrate the differences of cell sheets over manual seeding of electrospun matrices in terms of cell seeding efficiency and viability.

After combination of cell sheet and electrospun vascular scaffold at 1 day in culture, the cell sheet-vascular scaffolds were examined to assess the cell seeding efficiency and viability by staining with DAPI and TUNEL (see FIGS. 2A-2B). The same number of SMCs was used for the manual cell seeding for comparison. The cell sheet on the vascular scaffold showed a higher cell seeding efficiency when compared to manual cell seeding (n=3, *P<0.05) (see FIGS. 2A and 2C); however, there was no statistical difference in the initial cell viability between cell sheet engineering and manual cell seeding as confirmed by TUNEL staining Most of cells were identified viable from TUNEL staining after 1 day of culture (see FIGS. 2B and 2D).

FIGS. 2A-2D illustrate the advantages of cell sheets over manual seeding of electrospun matrices in terms of cell seeding efficiency and viability. The labeling molecule 4',6-diamidino-2-phenylindole (DAPI) is a fluorescent stain that binds strongly to A-T rich regions in DNA. Terminal deoxynucleotidyl transferase dUTP nick end labeling (TUNEL) is a method for detecting DNA fragmentation by labeling the terminal end of nucleic acids. FIGS. 2A-2B provide four micrographs illustrating DAPI (FIG. 2A) and TUNEL (FIG. 2B) staining of manual seeded matrices versus cell sheet/ electrospun laminous scaffolds at 1 day after seeding. FIG. 2C is a graph providing quantitative data of cell seeding efficiency and FIG. 2D is another graph showing the percentage of apoptotic cells after cell seeding by manual seeding or cell sheet methods (n=3, *P<0.05).

The phenotypes of SMCs were confirmed using immunofluorescent staining for α-SMA, CX43, and MLCK. The SMC sheet with vascular scaffolds showed strong expression of cell-to-cell junction and contractile proteins when compared with manual cell seeding (see FIG. 3A). Western blot quantification was used to detect SMC-specific proteins, α-SMA, CX43, and MLCK, in the SMC layers on the vascular scaffolds. The results indicated that the expression level of these proteins was significantly higher in the cell sheet-vascular scaffolds than in the manually cell-seeded vascular scaffold (n=3, *P<0.05) (see FIG. 3C). The results indicate that the cell sheet engineering significantly improved cell seeding efficiency and ECM protein expression while maintaining cell viability.

Figures 3A, 3B, 3C:
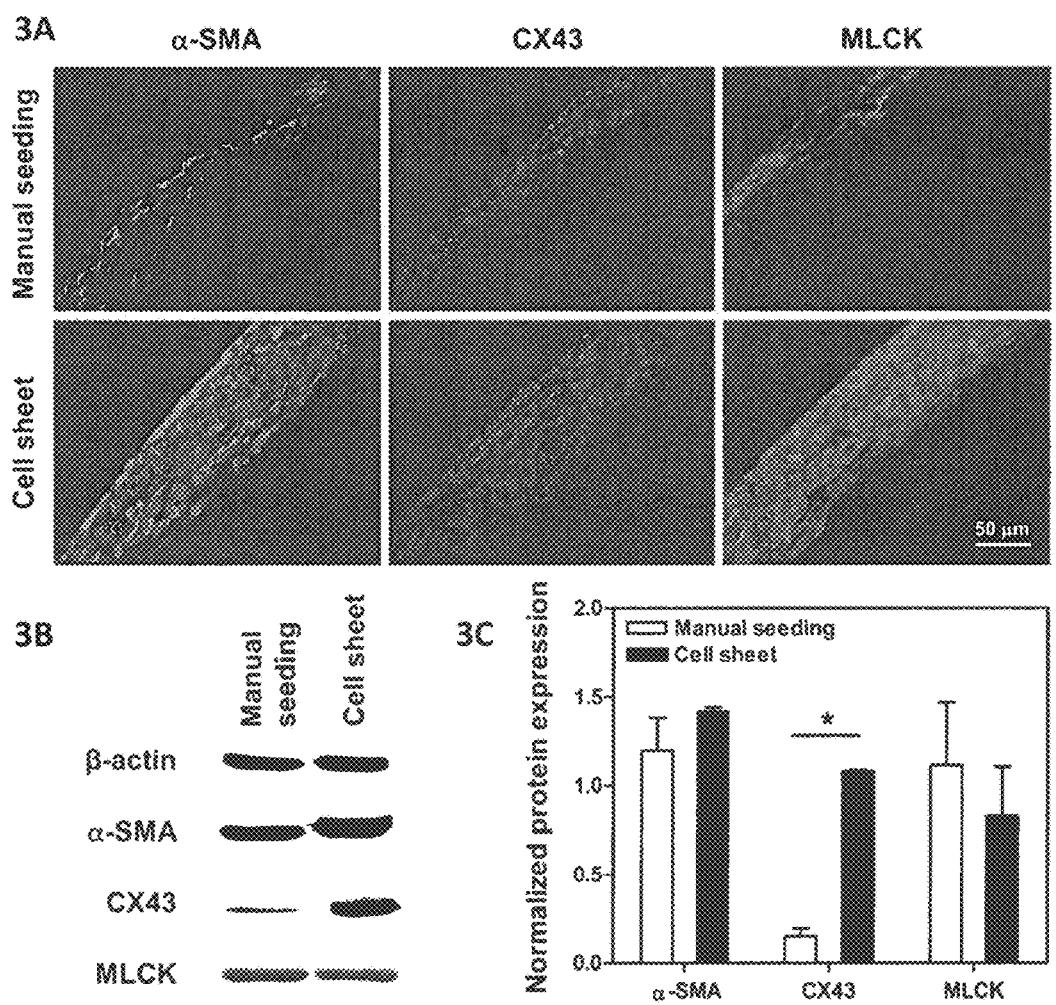
FIGS. 3A-3C provide further data of enhanced smooth muscle cell viability in laminous scaffolds according to one embodiment of the invention.

FIGS. 3A-3C provide further evidence of enhanced smooth muscle cell viability in laminous scaffolds according to the invention. FIG. 3A shows micrographs of the walls of a cellularized vascular scaffolds according to the invention. Immunofluorescent staining of cellularized vascular scaffolds for α-SMA, MLCK, and connexin 43 (CX43) is shown for a manual seeded construct (upper) and a smooth muscle cell sheet construct (bottom) after 5-day cell culture. FIG. 3C provides Western Blot analysis for the cell-seeded and vascular scaffolds by manual seeding and cell sheet methods.

Cellular Infiltration and Phenotypic Maintenance by Pulsatile Perfusion Bioreactor To improve the cellular infiltration and phenotypic maintenance, the SMC sheet-vascular scaffolds were dynamically stimulated by the pulsatile perfusion bioreactor system for 5 days. By increasing flow and amplitude, pulsatile stimulation achieved the conditions in a native artery. After 5 days of the pulsatile bioreactor, the structural integrity of the cell sheet remained with the vascular scaffold. Simultaneously, the SMCs from the cell sheet migrated into the vascular scaffold while maintaining the cell viability (see FIGS. 4A-4C). Cell sheet-vascular scaffolds under static culture conditions, however, showed no cellular infiltration into the scaffolds. Also, 96% of the fractions of SMCs were apoptotic as identified by TUNEL-positive cells (see FIG. 4C). The results indicate that the pulsatile perfusion bioreactor stimulation induced the cellular infiltration and maintained the cell viability during the period of the bioreactor condition.

Figures 4A, 4B, 4C:
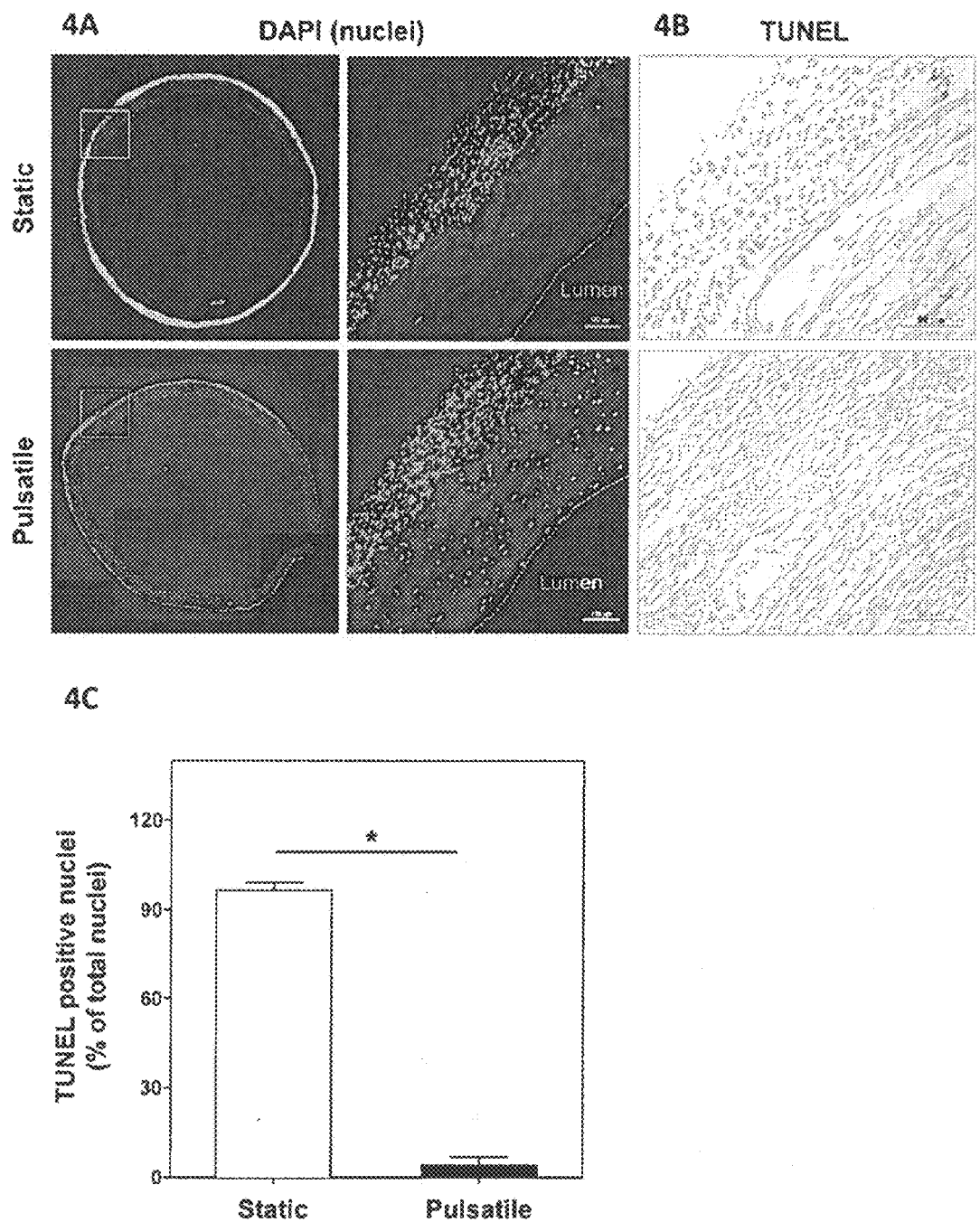
FIGS. 4A-4C illustrate cellular infiltration into the electrospun PCL/collagen scaffolds at 5 days of static and pulsatile preconditioning.

FIGS. 4A and 4B illustrate cellular infiltration into the electrospun PCL/collagen scaffolds at 5 days of static and pulsatile preconditioning. FIG. 4A shows DAPI staining and FIG. 4B shows TUNEL staining of the cell sheet-scaffolds at 5 days after static culture (upper panels) and preconditioning by pulsatile bioreactor (bottom panels). Dark staining indicated apoptotic cells. FIG. 4B is a graph of the percentage of TUNEL positive nuclei quantified by total nuclei (n=3, *P<0.05). Preconditioning process maintained cell viability and cellular infiltration into the scaffolds.

Figures 5A, 5B, 5C:
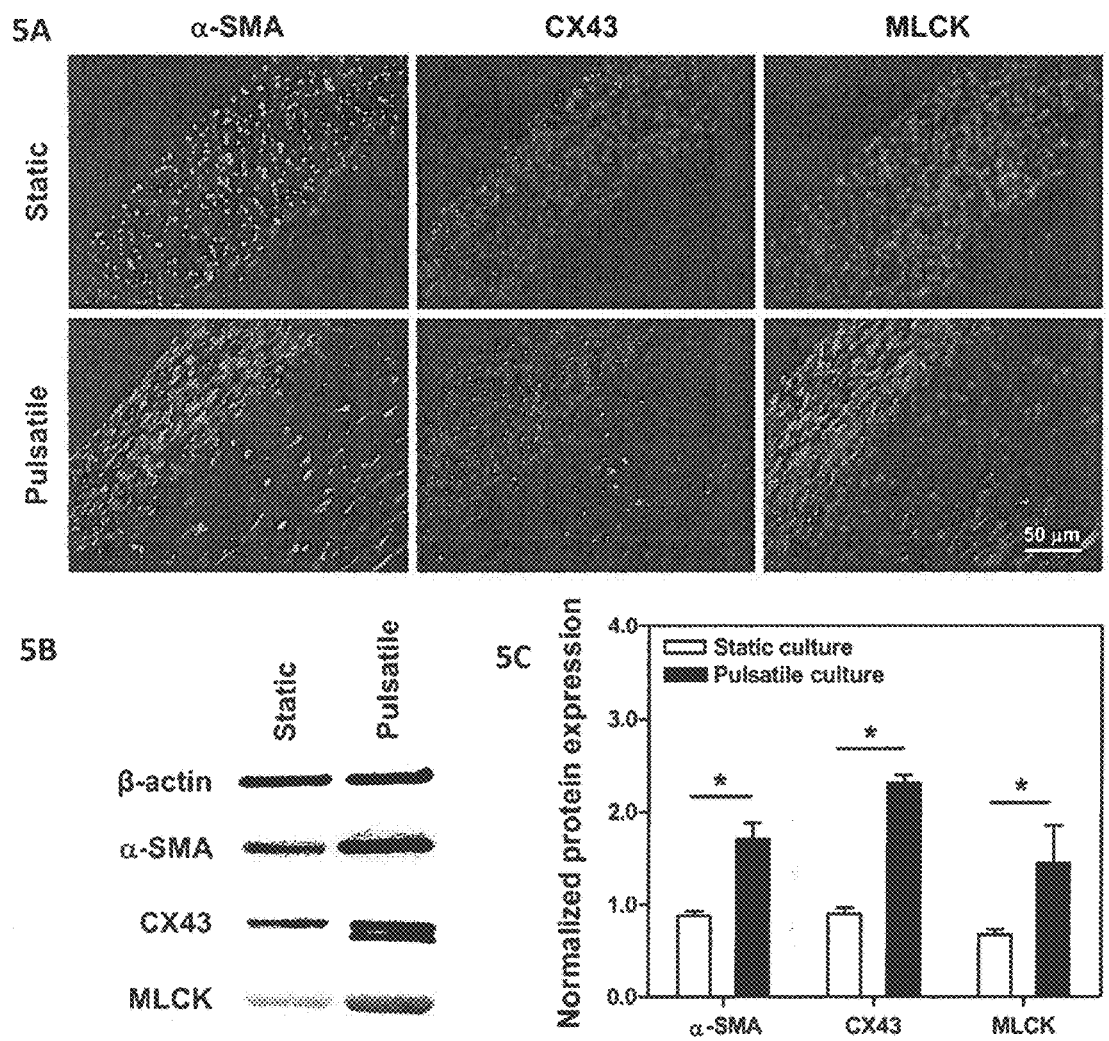
FIGS. 5A-5C provides SMC specific marker expression at 5 days after static culture or preconditioning by pulsatile bioreactor.
Figure 5D:
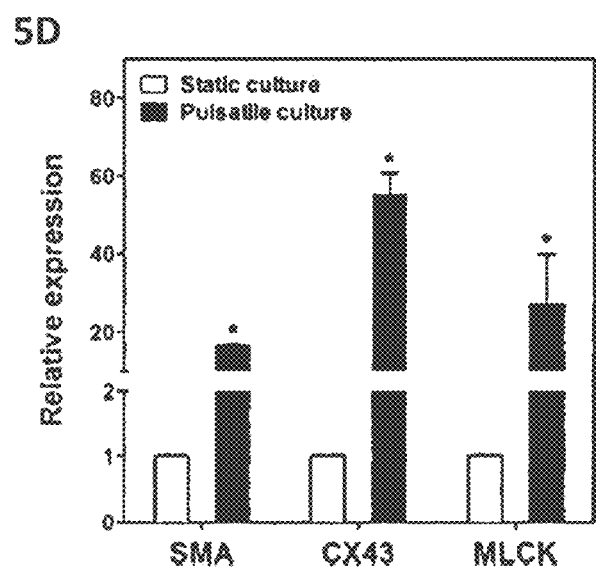
FIG. 5D provides qPCR analysis of the cell sheet vascular scaffolds.

Phenotypic expression of SMC markers, including α-SMA, CX43, and MLCK, was confirmed in the SM layer on the vascular scaffolds both under static culture and under pulsatile perfusion bioreactor (see FIGS. 5A-5D). Immunofluorescent images of cell sheet-vascular scaffolds under the pulsatile condition showed that SMCs strongly expressed all the SMC markers (FIG. 5A). CX43 expression showed a diffused pattern on entire layer of the vascular scaffold under the pulsatile conditions. CX43 was expressed on a limited site of the outer layer of the scaffold under the static conditions. Furthermore, expression of α-SMA and MLCK demonstrated aligned protein expression along with the fiber alignment of the vascular scaffolds under the pulsatile condition. Quantitative western blot analysis showed significantly increased SMC specific protein expression under the pulsatile conditioned scaffold compared with the static conditioned scaffold (n=3, *P<0.05) (FIGS. 5C and 5D). The results show that the pulsatile condition increased cellular infiltration into the scaffold while maintaining SMC phenotype and viability.

Primary SMCs were confirmed by the expression of α-SMA and SM-MHC. The electrospun vascular scaffold (5-micrometer fiber diameter) was able to combine with the fabricated smooth muscle cell sheet. As shown in FIGS. 5A-5D, the combination of cell sheet and electrospun vascular scaffolds enhanced expression of the mature SMC markers, including α-smooth muscle actin (α-SMA), connexin 43 (CX43) and myosin light chain kinase (MLCK), while statically cell-seeded scaffolds minimally expressed these markers. Moreover, preconditioning by the perfusion bioreactor maintained cell viability of SMC layer, while cell viability under the static culture condition decreased over time.

FIGS. 5A-5D provides SMC specific marker expression at 5 days after static culture or preconditioning by pulsatile bioreactor. FIG. 5A shows immunofluorescent staining of the cell sheet-vascular scaffolds. FIG. 5D provides qPCR analysis of the cell sheet vascular scaffold. FIGS. 5B and 5C show the Western Blot and quantitative data, respectively, for the cell sheet-vascular scaffolds (n=3, *P<0.05).

Tensile Properties of the SMC Sheet-Vascular Scaffolds

To examine whether the matured cell sheet contributed mechanical properties of the vascular scaffolds, tensile testing was performed using a uniaxial load test machine in circumferential direction on the vascular scaffolds before and after use of the pulsatile bioreactor. The tensile properties of the cell sheet-vascular scaffolds after the pulsatile bioreactor were significantly improved compared with the vascular scaffolds with the cell sheet (n=5, *P<0.05) (see FIGS. 7A-7D). The results indicate that the SM layer derived from cell sheet technology on the vascular scaffolds contributes to the mechanical properties of the vascular scaffolds.

Figure 7A:
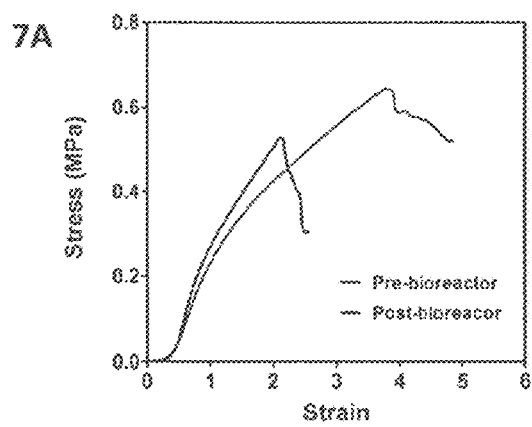
FIG. 7A provides stress-strain curves for the cell sheet vascular scaffolds before and after the pulsatile bioreactor.
Figure 7B:
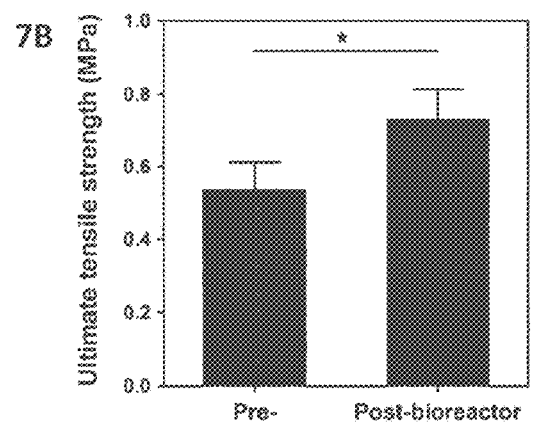
FIG. 7B is a graph of ultimate tensile strength for the cell sheet vascular scaffolds before and after the pulsatile bioreactor.
Figure 7C:
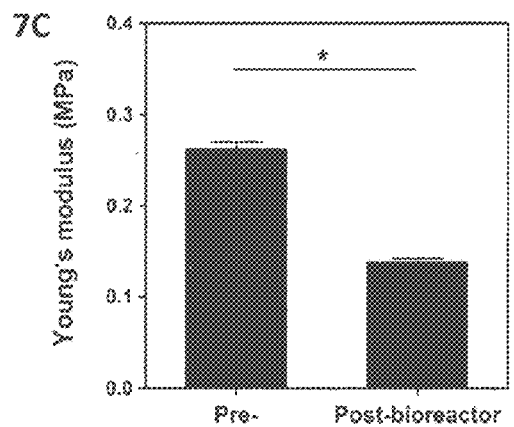
FIG. 7C is a graph of Young's modulus for the cell sheet vascular scaffolds before and after the pulsatile bioreactor.
Figure 7D:
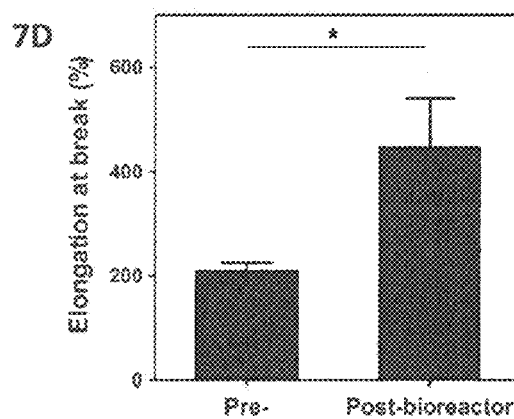
FIG. 7D is a graph illustrating elongation at break of the vascular scaffolds before and after the pulsatile bioreactor (n=3, *P<0.05).

FIGS. 7A-7D are graphs illustrating the results of the mechanical testing of composite cell sheet electrospun vascular scaffolds pre- and post-bioreactor. FIG. 7A provides stress-strain curves for the cell sheet vascular scaffolds. FIG. 7B is a graph of ultimate tensile strength for the cell sheet electrospun vascular scaffolds. FIG. 7C is a graph of Young's modulus for the cell sheet electrospun vascular scaffolds. FIG. 7D is a graph illustrating elongation at break of the cell sheet electrospun vascular scaffolds (n=5, *P<0.05).

Figure 6A:
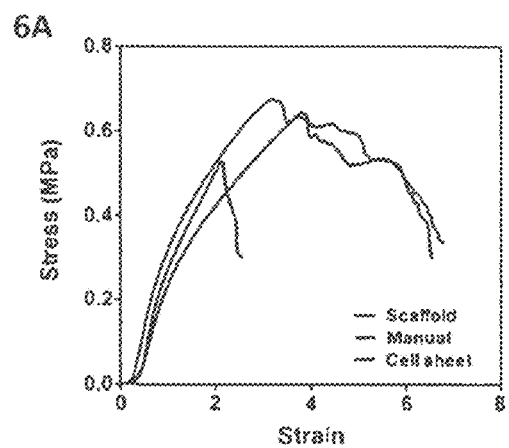
FIGS. 6A-6D are graphs illustrating the results of mechanical testing of naked electrospun tubular matrices, electrospun matrices manually seeded with SMCs and composite cellsheet/electrospun constructs according to one aspect of the present invention.
Figure 6B:
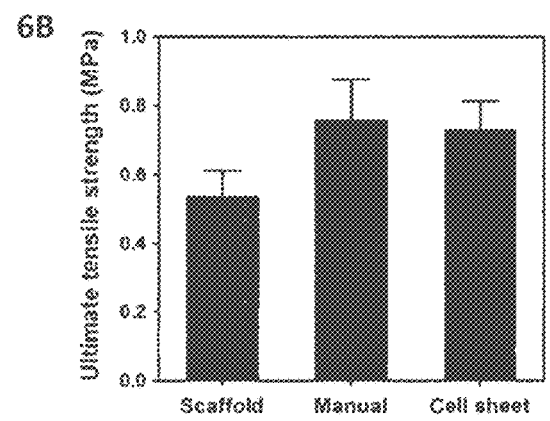
Figure 6C:
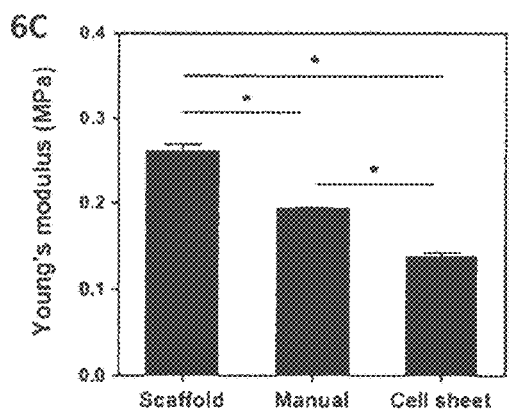
Figure 6D:
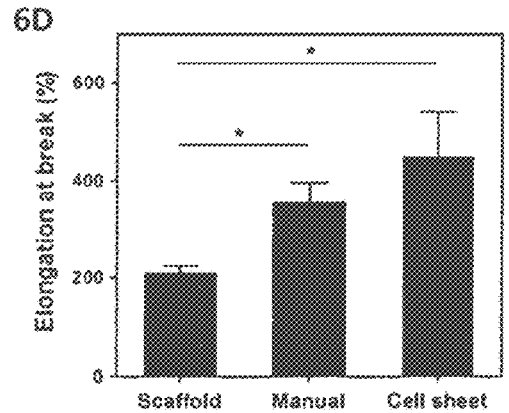

Referring to FIGS. 6A-6D, these graphs illustrate the results of mechanical testing of naked electrospun tubular matrices, electrospun matrices manually seeded with SMCs and composite cell sheet/electrospun constructs. FIG. 6A provides stress-strain curves for the three alternative structures (scaffold only v. manually seeded v. cell sheet wrapped). FIG. 6B is a graph of ultimate tensile strength for the three alternative structures. FIG. 6C is a graph of Young's modulus for the three alternative structures. FIG. 6D is a graph illustrating elongation at break of the vascular scaffolds (n=3, *P<0.05).

Discussion

The engineered vessels, described herein, were compliant, resistant to kinking and compression, and possessed sufficient tensile and shear strength to resist fraying at cut edges and tearing out of sutures. An electrospun vascular scaffold composite of synthetic PCL polymer and type I collagen was developed. This biodegradable tubular scaffold could withstand physiologically relevant vascular conditions over a period of one month in vitro. Further, this scaffold maintained its structural integrity after implantation in vivo in a rabbit aorto-iliac bypass model.

Vascular SMCs play an important role in the maturity of blood vessels. SMCs contribute to contractility and tone and accelerate tissue maturation providing mechanical stability for long-term patency. The presence of SMCs in a vascular implant can improve cellularization of the vascular graft, enhancing resistance to infection. Uniform and effective cell seeding is challenging due to the tubular shaped geometry of the vascular scaffolds. Cells can be seeded manually with a pipet on the exterior surface as the vascular scaffold is rotated. This process has shown limited cell adhesion and penetration into the vascular scaffolds, resulting in a low cell seeding efficiency. As described herein, a cell sheet engineering technique was combined with a pulsatile perfusion bioreactor. The cell sheet technique produced an intact sheet of cells without the need for enzymatic digestion. Using this approach, a viable monolayer cell sheet was collected with complete preservation of the cell-to-cell interactions and ECM proteins by a non-enzymatic process that controls the culture temperature to below 32° C. The cell sheet enabled a matured smooth muscle layer to be applied on a vascular scaffold surface and provided long-term patency and stability when transplanted in vivo.

The surface area of the harvested SMC sheets reduced to approximately 10% due to cellular contraction, resulting in densely packed thicker cell sheet layer. In addition, the harvested cell sheet can be transferred and stacked onto the first cell sheet to make multilayered cell sheets onto a tubular scaffold. As described herein, increased cell necrosis and apoptosis of the multilayered cell sheets on the vascular scaffold under the static culture condition was due to limitation of nutrition supply and gas exchange. As a result, most of cells in the cell sheets showed evidence of apoptosis and necrosis at 5 days of the static culture condition while the cell sheets under the pulsatile bioreactor condition maintained their viability (FIG. 4B).

As described herein, the dynamic culture environment developed by the pulsatile perfusion bioreactor increased the cell viability of the multilayered cell sheet on the vascular scaffolds by improving the nutrition supply and gas exchange. The pulsatile bioreactor perfused medium, aided in the transport of oxygen-rich medium and supported cellular metabolism through continuous nutrition supplementation. In addition, the pulsatile flow and pressure to the cell sheet-vascular scaffold regulated tissue maturity to withstand blood flow up to the level of the native artery. In fact, the pulsatile bioreactor system produced thicker scaffolds with increased protein expression, which correlated with the contractile characteristics of the SMCs (see FIGS. 5A-5D). The average thickness of the SMC sheet on the vascular scaffolds was 143.4 μm. The results suggest that the pulsatile bioreactor condition can be critical on cell survival and can be advantageous for vascular tissue engineering.

It has also been demonstrated that tissue maturation of the engineered vascular constructs can be enhanced by mechanical stimulation using a pulsatile perfusion bioreactor system prior to transplantation. Mechanical signals can accelerate cell and tissue growth, and phenotypic maintenance as well as protein production. In particular, the SMC layer stimulated by the pulsatile perfusion bioreactor was capable of forming a muscular layer on the vascular scaffolds and mobilizing calcium in response to cellular depolarization in vitro.

CONCLUSION

A tissue-engineered vascular constructs was fabricated by combining cell sheet engineering and electrospinning technology. Pre-fabricated SMC sheets were wrapped around the electrospun tubular scaffolds and provided a mature smooth muscle layer that expressed strong cell-to-cell junction and contractile proteins. Pulsatile perfusion bioreactor conditioning of the cell sheet-vascular scaffold improved cell viability and infiltration into the scaffold. This combined strategy provided a fully cellularized and matured vascular constructs that displayed prolonged biological and biomechanical stability when exposed to vascular physiological conditions in vivo.

Additional details on electrospinning and the fabrication and conditioning of electrospun vascular constructs can be found in U.S. Pat. No. 8,491,457 issued Jul. 23, 2013, entitled Tissue Engineered Blood Vessels. All patents and publications cited herein are expressly incorporated in their entirety by reference.

The present disclosure is not intended to be limited to a construct or method which must satisfy one or more of any stated or implied object or feature of the present disclosure and should not be limited to the preferred, exemplary, or primary embodiment(s) described herein. The foregoing description has been presented for purposes of illustration and description. It is not intended to be exhaustive or to limit the present disclosure to the precise form disclosed. Obvious modifications or variations are possible in light of the above teachings. All such modifications and variations are within the scope of the present disclosure as determined by the claims when interpreted in accordance with breadth to which they are fairly, legally and equitably entitled.

The invention claimed is:

1. A tissue engineered vascular construct, comprising:
an electrospun biocompatible matrix in a tubular configuration; and
a population of smooth muscle cells pre-fabricated as at least one smooth muscle cell sheet, the sheet comprised of smooth muscle cells grown to confluence on a substrate and then detached from said substrate as an intact sheet,
wherein the intact sheet is wrapped around the outside of the matrix to form a vascular construct.

2. The vascular construct of claim 1, wherein at least 2 cell sheets are applied to the outside of the matrix.

3. The vascular construct of claim 1, further comprising a population of endothelial cells seeding onto the inside the tubular matrix.

4. The vascular construct of claim 1, wherein the tubular matrix comprises at least one natural component from about 25 percent to about 75 percent by weight.

5. The vascular construct of claim 1, wherein the tubular matrix comprises an electrospun matrix comprising at least one natural component and at least one synthetic polymer component.

6. The vascular construct of claim 5, wherein the natural component comprises collagen.

7. The vascular construct of claim 5, wherein the synthetic polymer component comprises poly(ε-caprolactone) (PCL).

8. The vascular construct of claim 1, wherein the smooth muscle cells are derived from progenitor cells isolated from peripheral blood or bone marrow.

9. The vascular construct of claim 1, wherein the population of smooth muscle cells are cultured into one or more patterns.

10. The vascular construct of claim 1, further comprising a population of endothelial cells, applied to the inside of the matrix.

11. A tissue engineered vascular construct, comprising:
an electrospun biocompatible matrix in a tubular configuration comprising at least one natural component and at least one synthetic polymer component, wherein the natural component comprises collagen and wherein the synthetic polymer component comprises poly(ε-caprolactone) (PCL); and
a population of smooth muscle cells pre-fabricated as at least one smooth muscle cell sheet, the sheet comprised of smooth muscle cells grown to confluence on a substrate and then detached from said substrate as an intact sheet,
wherein the intact sheet is wrapped around the outside of the matrix to form a vascular construct.

12. The vascular construct of claim 11 wherein at least an outer portion of the tubular matrix has fibers that are oriented in a circumferential manner to mimic the orientation of SMCs in native vessels.

13. A method of producing a tissue engineered vascular construct as recited in claim 1, comprising:
forming an electrospun biocompatible matrix in a tubular configuration;
culturing a cell population comprising smooth muscle cells to form a cell sheet and applying the cell sheet to the outside of the matrix to form a vascular construct.

14. The method of claim 13, wherein at least two cell sheets are applied to the outside of the matrix to form the vascular construct.

15. The method of claim 13, further comprising seeding the inside of the matrix with a population of endothelial cells.

16. The method of claim 13, wherein the tubular matrix comprises at least one natural component from about 25 percent to about 75 percent by weight.

17. The method of claim 13, wherein the tubular matrix comprises an electrospun matrix comprising at least one natural component and at least one synthetic polymer component.

18. The method of claim 17, wherein the natural component comprises collagen.

19. The method of claim 17, wherein the synthetic polymer component comprises poly(ε-caprolactone) (PCL).

20. The method of claim 13, further comprising:
attaching a first end and a second end of the vascular construct to a first attachment and a second attachment element in a preconditioning chamber, wherein the first attachment and the second attachment elements each have a channel that is fluidly coupled to a fluid flow system; and
preconditioning the construct with the flow system by moving a biological fluid through the construct, wherein a flow-rate and a pulse-rate of the biological fluid is controlled such that a preconditioned vascular construct is produced.

21. The method of claim 20, wherein the step of preconditioning the construct comprises moving the biological fluid through an inside surface of the seeded tubular matrix in a closed fluid flow system.

22. The method of claim 20, wherein the step of preconditioning the seeded tubular matrix further comprises moving a biological fluid having a composition and viscosity that mimics blood through the inside surface of the attached matrix as a pulsed flow to induce a wall shear stress of at least 10 dynes/cm$^2$ so that the vascular construct is exposed to fluid flow conditions that mimic flow of blood through a native blood vessel.

23. The method of claim 22, further comprising continuing exposure of the cells on the inside surface of the matrix to the pulsed fluid flow to allow the seeded cells to develop under fluid flow conditions until the matrix can withstand a wall pressure distribution of at least 60 mmHg.

24. The method of claim 20, wherein the pulsed flow has a pulse-rate that is varied over time to induce a wall shear stress in the range of about 10 dynes/cm$^2$ to about 45 dynes$^2$.

25. The method of claim 20, wherein the pulsed flow has a pulse-rate that is varied over time to induce a wall pressure distribution in the range of about 60 mmHg to about 200 mmHg.

26. The method of claim 20, wherein the biological fluid is moved through the seeded tubular matrix by a pump.

27. The method of claim 13, wherein the smooth muscle cells are derived from progenitor cells isolated from peripheral blood or bone marrow.

* * * * *